(12) United States Patent
Neuffer

(10) Patent No.: US 9,778,170 B2
(45) Date of Patent: Oct. 3, 2017

(54) METHOD AND APPARATUS FOR DETERMINING A BARRIER EFFECT OF A COATING ON A SUBSTRATE

(71) Applicant: Carl Zeiss Vision International GmbH, Aalen (DE)

(72) Inventor: Andreas Neuffer, Asperg (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 15/470,537

(22) Filed: Mar. 27, 2017

(65) Prior Publication Data

US 2017/0199112 A1    Jul. 13, 2017

Related U.S. Application Data

(63) Continuation of application No. PCT/EP2015/071474, filed on Sep. 18, 2015.

(30) Foreign Application Priority Data

Sep. 26, 2014    (DE) .......................... 10 2014 219 496

(51) Int. Cl.
   *G01N 19/06* (2006.01)
   *G01B 21/08* (2006.01)

(52) U.S. Cl.
   CPC .............. *G01N 19/06* (2013.01); *G01B 21/08* (2013.01)

(58) Field of Classification Search
   CPC ........ G01N 19/16; G01N 21/08; G01B 21/18; G01B 21/02

(Continued)

(56) References Cited

U.S. PATENT DOCUMENTS

| 5,729,323 A | 3/1998 | Arden et al. |
| 6,658,919 B2 | 12/2003 | Chatard |

(Continued)

FOREIGN PATENT DOCUMENTS

| DE | 19519975 C1 | 10/1996 |
| DE | 102013104846 B3 | 6/2014 |

OTHER PUBLICATIONS

International Search Report dated Dec. 15, 2015 of international application PCT/EP2015/071474 on which this application is based.

(Continued)

*Primary Examiner* — Daniel S Larkin
*Assistant Examiner* — Anthony W Megna Fuentes
(74) *Attorney, Agent, or Firm* — Walter Ottesen, P.A.

(57) ABSTRACT

Determining a barrier effect of a coating for a medium includes: providing a substrate having the coating on its surface, the substrate undergoing a volume change on contact with the medium; conditioning the substrate with the coating; removing the coating from a first part of the surface, leaving the coating on a second part, the first part having an extent in a first direction delimited by the coating remaining on the second; determining a height profile of the coating on the second part and the first part on a path in the first direction; exposing the remaining coating and the first part to the medium; determining a second height profile of the coating on the second part and the first part on the path in the first direction and/or determining a difference in height profile on the second and first part with respect to the height profile determined beforehand.

16 Claims, 7 Drawing Sheets

(58) Field of Classification Search
USPC .................................................. 73/150 R, 7
See application file for complete search history.

(56) References Cited

U.S. PATENT DOCUMENTS 8,266,944 B2    9/2012   Kwon et al.
8,982,466 B2    3/2015   Neuffer

OTHER PUBLICATIONS

Translation and Written Opinion of the international searching authority dated Mar. 31, 2016 of international application PCT/EP2015/071474 on which this application is based.
International Preliminary Report on Patentability dated Mar. 28, 2017 of international application PCT/EP2015/071474 on which this application is based.

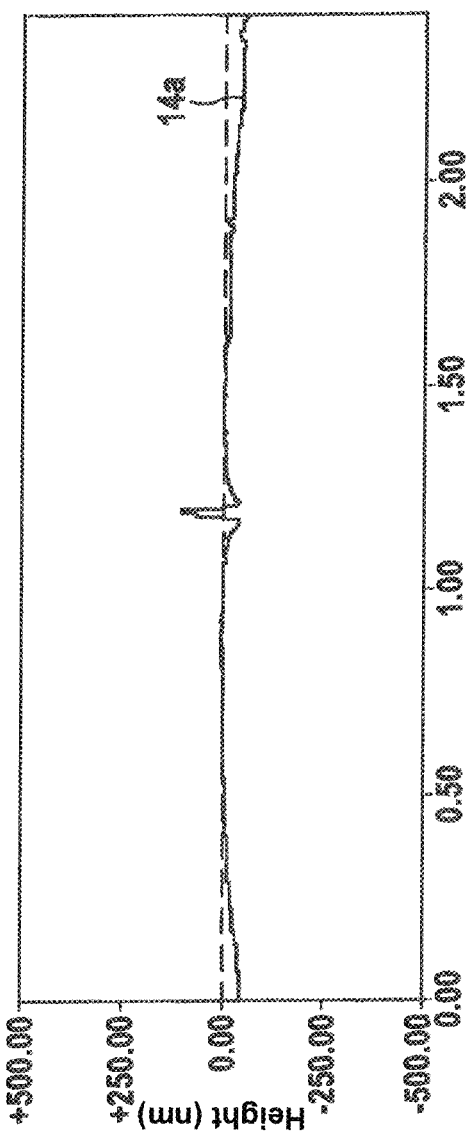
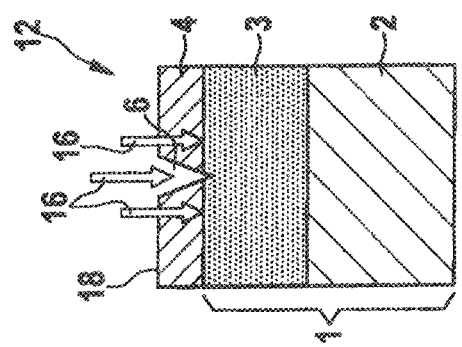
Fig. 7B
Fig. 7A

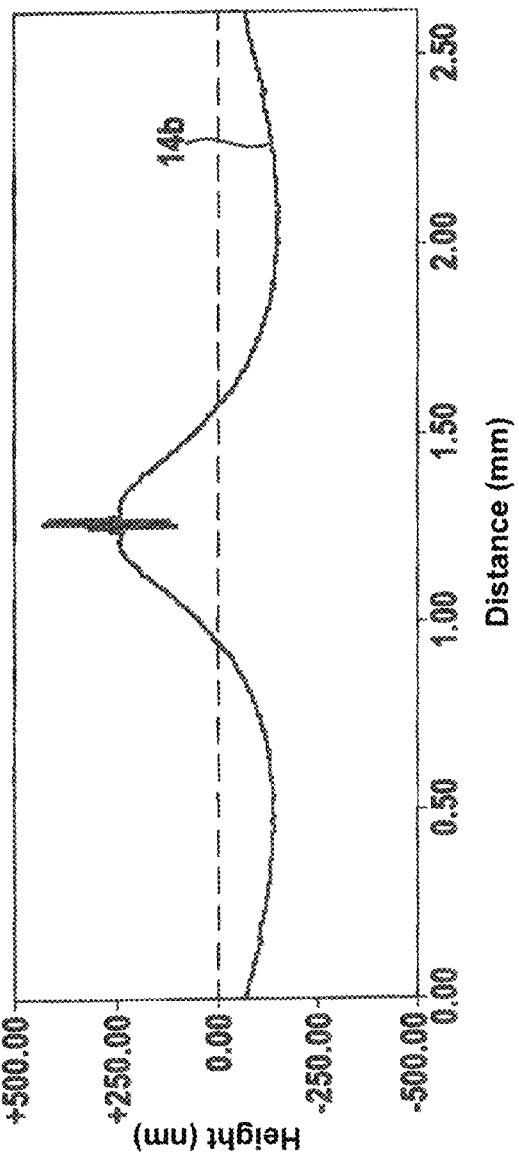

METHOD AND APPARATUS FOR DETERMINING A BARRIER EFFECT OF A COATING ON A SUBSTRATE

CROSS REFERENCE TO RELATED APPLICATION

This application is a continuation application of international patent application PCT/EP2015/071474, filed Sep. 18, 2015, designating the United States and claiming priority from German application 10 2014 219 496.2, filed Sep. 26, 2014, and the entire content of both applications is incorporated herein by reference.

FIELD OF THE INVENTION

The invention concerns a method for determining a barrier effect of a coating on a substrate, and an apparatus or device for determining a barrier effect of a coating on a substrate.

BACKGROUND OF THE INVENTION

In materials science, a substrate is understood to refer to a material to be treated. The surface of the substrate is often processed or coated. In the present patent application, the substrate includes the body having a coating whose barrier effect is to be determined. The substrate can therefore include in particular a base body made of a homogeneous material to which a coating has already been applied but is itself not intended to be the object of testing of the barrier effect thereof.

The term coating is understood in production technology to refer to a main group of the production processes according to DIN 8580 that are used to apply a firmly adhering layer of amorphous material to the surface of a workpiece. The term coating denotes both the corresponding process and the applied layer itself. A coating may be made of a thin or thick layer or a plurality of interconnected layers. Coating methods are classified according to the type of layer application into chemical, mechanical, thermal, and thermomechanical methods.

A barrier is understood in the present patent application to refer to an obstacle. Accordingly, a barrier effect of a coating is a measure of the effect of the coating as an obstacle to a medium. Such a medium may be a fluid, that is, a gas or a liquid.

The invention concerns a method via which the barrier qualities of layers, in particular vapor-deposited layers (for example layers applied via physical gas-phase deposition or physical vapor deposition, PVD), layers deposited via chemical reactions (for example by plasma enhanced chemical vapor deposition, PECVD or plasma induced chemical vapor deposition, PICVD), layers applied by cathode deposition or sputtering, or galvanically deposited layers or lacquer layers that can be measured and quantitatively evaluated on a suitable substrate.

A method for measuring the gas permeability of a coating on a plastic wall is known from U.S. Pat. No. 6,658,919. U.S. Pat. No. 8,266,944 B2 describes a method for evaluating the scratch resistance of a plastic resin.

Especially in the area of plastic coatings, particularly in the area of coating of plastic spectacle lenses with nonreflective coatings, it is known that under the effect of moisture, plastics can absorb this moisture from the environment and thus increase their volume. In cases where a non-moisture-permeable coating is present on the plastic, this leads to local areas of swelling referred to as distortions that warp the surface of the coated (tempered) plastic to such an extent that this can be observed as optical interference.

A method is known from company-internal prior art and DE 10 2013 104 846 B3 for the measurement of the barrier qualities of such plastic/coating systems with respect to moisture in which the water content of the plastic substrate is measured via infrared absorption in order to then calculate the transmission factor of water through the layer system located on the plastic. However, this infrared measurement technique is only an indirect method with respect to the distortions occurring on penetration of water, and it cannot provide any data on the swelling behavior of the plastic.

SUMMARY OF THE INVENTION

It is an object of the invention to provide a method and a device via which quantitative data can be obtained on the barrier qualities of a coating applied to a substrate, in particular a plastic, and via which the swelling behavior of the substrate, in particular the plastic, can be quantitatively determined together with the coating.

The object of the invention can, for example, be achieved by a method for determining a barrier effect of a coating for a medium. The method includes the steps of: a) providing a substrate with the coating on its surface, which on contact with the medium undergoes a change in volume, or providing the coating on a surface of a substrate, which on contact with the medium undergoes a change in volume; b) conditioning of the substrate with the coating; c) removing the coating from a first part of the surface of the substrate, with the coating remaining on a second part of the surface of the substrate, and with the first part of the surface having an extension (L) in a first direction delimited by the coating remaining on the second part of the surface; d) determining a first height profile of a surface of the coating remaining on the second part of the surface and the first part of the surface of the substrate on a path in the first direction; e) exposing the surface of the remaining coating and the first part of the surface of the substrate to the medium; and, f) determining at least one of a second height profile of the surface of the coating remaining on the second part of the surface and the first part of the surface of the substrate on the path in the first direction and a first height profile difference (H) of the surface of the coating remaining on the second part of the surface and the first part of the surface of the substrate on the path in the first direction with respect to the previously-determined height profile.

The method for determining a barrier effect of a coating for a medium requires that the coating be located on a surface of a substrate that undergoes a change in volume, in particular an increase or optionally also a decrease in volume, when it comes into contact with the medium. The method for determining a barrier effect of a coating for a medium includes the following steps:

In step a), the coating is first provided on a surface of a substrate, which on contact with the medium undergoes a change in volume, in particular an increase in volume. Alternatively, a substrate can also be provided in step a) with the coating on its surface, which on contact with the medium undergoes a change in volume.

The substrate may for example be a spectacle lens blank composed of a plastic material. For production of spectacle lenses, for example, plastic materials with the brand names MR 7, MR 8, MR 10 and CR 39, CR 607, and CR 630 are used. The plastic materials with the brand names MR 7, MR 8, and MR 10 are polythiourethanes marketed by Mitsui Chemicals. Here, the abbreviation "MR" stands for Mitsui Resin. CR 39 or Columbia Resin 39 is the brand name selected by Pittsburgh Plate Glass Industries (PPG Industries) under which the material polydiethylene glycol bis (allyl carbonate) or poly(allyldiglycol carbonate) (abbreviation: PADC) is marketed. This is a highly-refractive duroplastic polymer material. CR 607 and CR 630 are also produced by PPG. The materials CR 607 and CR 630 are used for example for photochromic applications.

The substrate need not be present only in the form of a volume material. Moreover, it does not necessarily have to be composed of homogeneous material. Rather, it is possible for the substrate to be made of a basic material having a coating. Continuing with the above-described example, the substrate may be a spectacle lens blank made of a plastic base body and a hard lacquer coating.

The medium may for example be water in liquid form or in the form of water vapor, that is, in gas form. In the above-described case of testing a spectacle lens blank as a substrate in particular, testing of the barrier effect can be of significance with respect to fats, oils, and corrosive liquids or vapors.

A main application of the method according to the invention is testing of the penetration behavior of the medium after previous transmission through the coating on the substrate. However, it is also suitable for use in testing of the medium-induced transmission behavior of components of the substrate (in the opposite direction) through the coating.

In the case of the spectacle lens blank, the coating can be a nonreflective or antireflective coating. Alternatively, or optionally by spectrum selection in addition, the coating may also be a reflective coating. The coating may additionally or alternatively be a coating having an antistatic effect. The coating may be an anti-scratch or hard coating. The coating may be a coating that prevents or at least reduces steaming up with water vapor. The coating may have a photochromic, phototropic, or electrochromic function.

In a further step b), the substrate with the coating is conditioned. In the present invention, the term conditioning refers to treatment of the substrate with the coating in order to produce or prepare a specified and/or reproducible baseline state for the following steps.

Conditioning is understood in plastics technology in particular to refer to storage until weight equilibrium (weight constancy) is reached due to water absorption in a standardized climate (23° C. and 50% relative humidity). This conditioning process is reversible here.

In the above-described example of testing of a plastic spectacle lens in a humid environment, it is not absolutely necessary to carry out storage in a standardized climate that is common in plastics technology. Other climatic conditions tailored to the purpose of use can also be used.

In a following step c), the coating is removed from a first part of the surface of the substrate. In this case, the coating is left unchanged on a second part of the surface of the substrate. The coating need not necessarily be removed completely all the way to the surface of the substrate. A portion of the coating can by all means remain intact in a normal direction relative to the substrate surface. The extension of the first part of the surface in a first direction is here delimited by the coating remaining on the second part of the surface. The function of removing the coating is to provide complete or facilitated passage of the medium, in particular moisture or water, with which the system, for example the plastic spectacle lens blank and coating, is tested for barrier qualities and swelling behavior.

Step d) includes determination of a first height profile of a surface of the coating on the second part of the surface and the first part of the surface of the substrate on a path in the first direction.

After this, in a step e), the surface of the remaining coating and the first part of the surface of the substrate are exposed to the medium. In the above-described example, the plastic substrate-coating system can be placed in a correspondingly humid atmosphere, for example in a climatic chamber under a temperature of 40° C. and relative humidity of 90%, so that swelling can occur. The duration of exposure of the prepared coated substrate to the medium is preferably predetermined in order to achieve, to the greatest extent possible, specified and thus comparable conditions.

A further step f) includes determination of a second height profile of the surface of the coating on the second part of the surface and the first part of the surface of the substrate on the path in the first direction and/or determination of a first height profile difference of the surface of the coating on the second part of the surface and the first part of the surface of the substrate on the path in the first direction with respect to the predetermined height profile. This makes it possible to detect changes in the surface and obtain a measure of the swelling behavior of the substrate and thus the barrier effect of the coating.

Accordingly, the object indicated above is fully achieved by the method according to the invention.

It has been found that removal of the coating according to step c) can be carried out very quickly using a scratching tool, in particular a diamond scratching tool, which is guided in the first direction to remove material. A diamond has a defined tip radius, and the load can be set in a specified manner. This ensures the reproducibility of the method according to the invention and the quantitative comparability of the results.

In particular, the coating is removed in the case of the above-described testing of a spectacle lens blank made of a plastic optionally coated with a hard lacquer preferably via a scratching tool having a cutting diameter in the nanometer range, referred to as a nano-scratcher. This ensures that even in comparison of layers having differing hardness and/or differing porosity, there is no difference in the dimensions or extensions of the areas in which the coating is removed.

Experiments have shown that reproducible results can be achieved if the first part of the surface from which the coating is removed has an elongated form. In this case, the first part of the surface has the above-described extension in the first direction and an extension in a second direction. The extension of the first part of the surface in the first direction is preferably at least 10 times greater than the extension of the first part of the surface in the second direction. In other words, the length of the scratch is at least 10 times the width of the scratch. It is even more favorable if the scratch length is between 10 and 100 times larger than the scratch width.

In the case of the spectacle lens blank with the coating, the load applied with the diamond tool should be great enough so that the coating to be tested reliably breaks and the trace on the coating is also optically visible.

In order to prevent the medium from penetrating the substrate via areas other than the first part of the surface or the surface provided with the coating, these other areas, subsequently referred to as the third part of the surface, can be provided in advance with a barrier that is impermeable to the medium. In other words, prior to determination of the first height profile according to step d), the third part of the surface that is not identical to the first part of the surface of the substrate but does not have the coating can be provided with a barrier that is impermeable to the medium.

In the case of the above-described example of a coated plastic spectacle lens blank, for example, after the scratch is made using the diamond scratching tool, the uncoated rear side of the spectacle lens blank is sealed in a watertight manner, for example with aluminum foil.

The measuring device that can be used for determining a height profile or a height profile difference is determined based on the extent of the expected swelling behavior of the substrate and the extension of the area in which the coating was removed.

In the example of the spectacle lens blank/coating system, the scratch length is generally a few millimeters, and the expected distortion height is in the two- to four-digit nanometer range. In a case of this type, determination of the first height profile according to step d) and/or determination of the second height profile and/or the first height profile difference according to step f) is preferably carried out using an interferometer. The preferred interferometer has a resolution via which the height can be measured over the entire scratch length, specifically a resolution that is at least less than 10 nm.

It is possible in principle to obtain an initial finding for the above-mentioned quantitative data after carrying out all of the above-described process steps only once. Nevertheless, it has been found to be preferable if the series of steps e) and f) is carried out repeatedly. In this manner, one can obtain quantitative data on the course of swelling behavior over time.

It is further preferred for the series of steps e) and f) to be carried out repeatedly until a termination criterion is fulfilled. A termination criterion can be met, for example, if the measurement series is continued up to the point in time at which virtually no more change in the swelling behavior of the substrate can be detected.

For example, the latter condition can be expressed if the termination criterion is that the first height profile difference must be below a specified threshold value.

As indicated above, the extent of removal of the coating is not decisive for the applicability of the method. As expected, however, it has been found to be advantageous when removal of the coating in step c) is carried out completely down to the surface of the substrate, because this allows reproducible and comparable conditions to be achieved with relatively low expense.

Alternatively, however, the inventor found that a method in which the series of steps c) through f) is repeatedly carried out locally in parallel and removal of the coating in the respective steps c) in the series carried out locally in parallel is carried out to differing degrees is advantageous. Specifically, this method makes it possible to obtain data on the breaking load behavior of the coating.

In the latter method in particular, it is preferable when removal of the coating in the respective steps c) in the series carried out locally in parallel is carried out under differing loads. This allows the depth of the scratches to be varied.

If removal of the coating in at least one of the respective steps c) in the series carried out locally in parallel is carried out all the way to the surface of the substrate, this ensures that the medium can penetrate the substrate and/or come into contact with the substrate and swelling (or optionally shrinking) can occur.

If removal of the coating in at least one of the respective steps c) in the series carried out locally in parallel is not carried out all the way to the surface of the substrate, complete tearing of the layer can be brought about by deforming the substrate under a load in the area of at least one of the scratches that originally did not extend down to the substrate surface, thus allowing direct contact between the substrate and the medium.

A method according to the invention can be implemented in a computer-controlled manner. In particular, the invention includes a computer program with program code for carrying out all of the process steps in one of the above-described variants when the computer program is loaded onto a computer and/or run on a computer.

The invention also concerns a device for determining a barrier effect of a coating. The device includes the following components:

There is a provision device for provision of the coating on a surface of a substrate or for provision of a substrate with the coating on its surface, which on contact with the medium undergoes an increase in volume. The provision device can include a supporting surface to which an operator has applied the substrate with the coating. There can also be a holding device for detachably holding the substrate with the coating in a specified position in order to carry out the following process steps.

A device according to the invention includes a conditioning device for conditioning of the substrate with the coating in the above-described manner. The conditioning device may include a climatic chamber or include such a chamber, in which for example the relative humidity, temperature, and duration of exposure can be predetermined.

A removal device for removal of the coating from a first part of the surface of the substrate is provided, so that the coating remains on a second part of the surface of the substrate and so that the first part of the surface has an extension in the first direction delimited by the coating remaining on the second part of the surface. As described above, the removal device can be configured as a scratching tool, in particular a diamond scratching tool.

Moreover, a determination device for determination of a first height profile of a surface of the coating on the second part of the surface and the first part of the surface of the substrate on a path in the first direction is provided. This determination device preferably includes an interferometer. Preferably, the interferometer should have a resolution of less than 10 nm.

Moreover, an exposure device is provided for exposure of the surface of the remaining coating and the first part of the surface of the substrate to the medium. This exposure device may be identical to the above-described conditioning device, and in particular may be configured as a climatic chamber with the above-described setting possibilities.

Finally, a determination device is provided for determination of a second height profile of the surface of the coating on the second part of the surface and the first part of the surface of the substrate on the path in the first direction and/or for determination of a first height profile difference of the surface of the coating on the second part of the surface and the first part of the surface of the substrate on the path in the first direction with respect to the previously-determined height profile. This may be identical to the determination device for determination of the first height profile. In particular, it can be configured as an interferometer with a resolution of less than 10 nm.

A conveying device may be provided that is configured to transport the substrate with the coating on the provision device (for example supporting surface) to the conditioning device (for example climatic chamber), the removal device (for example scratching tool), the exposure device (for example climatic chamber), and the determination device (for example interferometer) according to at least one of the above-described methods. For example, the device includes a control device for controlling the conveying device and optionally the functions of the other components.

The device may be controlled by a computer. For this purpose, a computer program is provided with program code for carrying out all of the above-described process steps in an above-described device, when the computer program is loaded onto the computer and/or run on the computer that controls the device.

BRIEF DESCRIPTION OF THE DRAWINGS

The invention will now be described with reference to the drawings wherein:

FIG. 7A shows exposure of the spectacle lens blank according to FIG. 5 to a warm, humid climate in a schematic representation according to FIG. 1, with the coating not constituting a barrier to moisture;

FIG. 7B shows a height profile of the surface of the spectacle lens blank perpendicular to the scratch, measured after the exposure shown in FIG. 7A;

FIG. 8A shows exposure of the spectacle lens blank according to FIG. 5 to a warm, humid climate in a schematic representation according to FIG. 1, with the coating having a certain barrier effect with respect to moisture;

FIG. 8B shows a height profile of the surface of the spectacle lens blank perpendicular to the scratch, measured according to the exposure shown in FIG. 8A after saturation was reached;

DESCRIPTION OF THE PREFERRED EMBODIMENTS OF THE INVENTION

Figure 1:
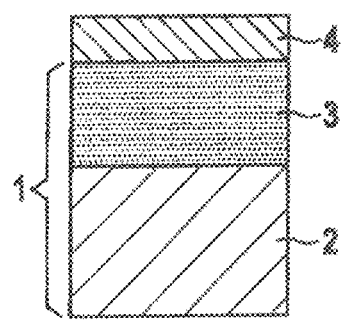
FIG. 1 shows a section of a substrate made of a plastic base body provided with a hard lacquer and an nonreflective coating on the substrate shown in a cross-sectional view.

FIG. 1 shows a section of a substrate 1 made of a plastic base body 2 provided with a hard lacquer 3 and a nonreflective coating 4 on the substrate 1 in a cross-sectional view. In the present illustrative embodiment, the section is a component part of a spectacle lens blank according to prior art. In principle, this could also be the section of an architectural glass window.

The plastic base body 2 in the present illustrative embodiment may be an organic plastic such as poly(allyl diglycol carbonate). The hard lacquer 3 is generally composed of an inorganic plastic such as polysiloxane with optionally highly-refractive components, and the nonreflective or antireflective coating may consist, for example, of a series of layers as described in U.S. Pat. No. 8,982,466. This spectacle lens blank is provided according to step a) described above.

Determination of the barrier behavior of this coating 4 applied to the plastic substrate 1 made of an organic plastic base body 2 and a hard lacquer coating 3 initially requires a few days before conducting measurements of exposure or storage in a specified climate, for example at room temperature and average relative humidity of for example 50% in order to obtain a constant specified starting point for subsequent measurements. The duration of exposure is selected in such a way that a change in the state of the plastic substrate 1/coating 4 system is not to be expected in continuing exposure or is negligibly small. This step is also referred to as conditioning (cf. step b).

Figure 2:
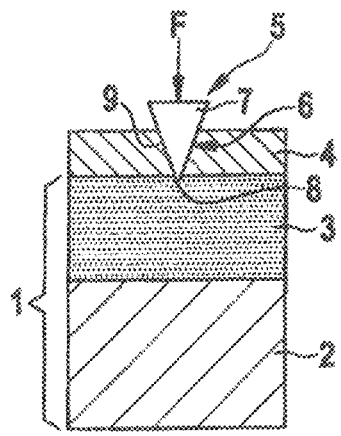
FIG. 2 shows removal of the nonreflective coating from a first part of the surface of the substrate using a diamond scratching tool shown schematically with respect to the section according to FIG. 1.

Next, a diamond scratching tool 5 referred to as a nanoscratcher 5 is used to make a scratch 6 as shown schematically in FIG. 2. The tip 8 of the diamond 7 has a known tip radius. The "scratch 6" is made with a specified load F (cf. step c) above). Ordinarily, the load F in the case of the described system is 50 mN with a tip radius of 2 µm.

Figure 3:
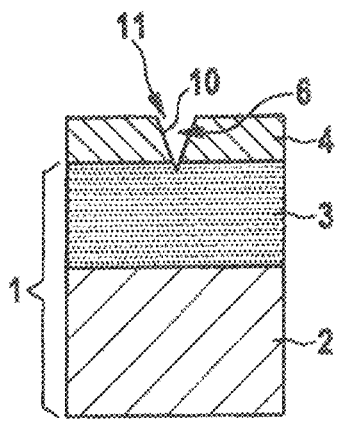
FIG. 3 shows the section according to FIG. 1 after the diamond scratching tool for removing the nonreflective coating of the first part of the surface of the substrate has been guided in a direction perpendicular to the plane of the drawing.

FIG. 3 shows the section according to FIG. 1 after the diamond scratching tool 5 for removing the nonreflective coating 4 from the surface 11 of the substrate 1 was guided in a direction perpendicular to the plane of the drawing. The cross-sectional contour 10 of the scratch 6 ideally corresponds to the cross-sectional contour 9 of the diamond scratching tool 5.

Figure 4:
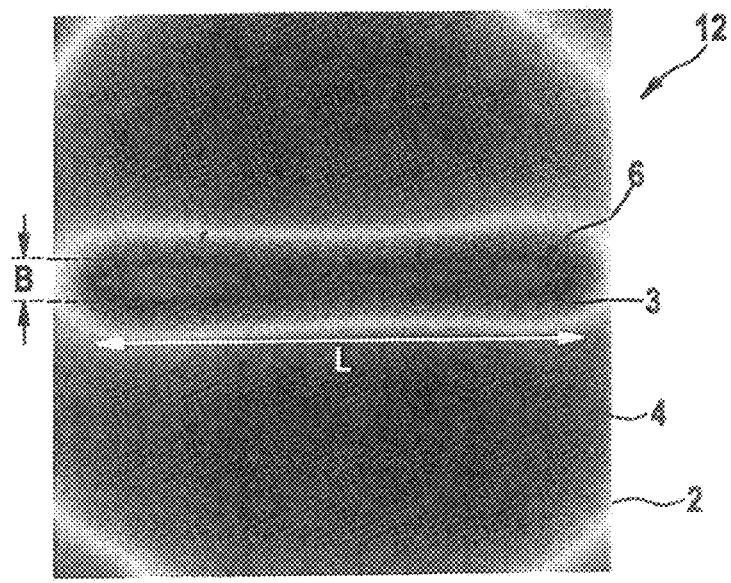
FIG. 4 is a top view of a section of a spectacle lens blank made of a plastic base body composed of CR 39 with a hard lacquer and an nonreflective coating that is provided with a scratch according to step c) of a method according to the invention.

FIG. 4 shows a top view of a section of a spectacle lens blank 12 made of a plastic base body 2 composed of CR 39 with hard lacquer 3 and a nonreflective coating 4, which was provided with a scratch 6 according to the above-described process step c).

The length L of the "scratch 6" should be at least ten times as long as the width B of the "scratch 6", but preferably between 10 times and 100 times the scratch width B. The scratch length L in the present illustrative embodiment is 2.5 mm. The scratch width B is 0.2 mm. The Load F shown in FIG. 2 must be great enough that the coating 4 to be tested reliably breaks and the trace or the course of the scratch 6 on the coating 4 can also be optically observed (FIGS. 3 and 4).

The function of the "scratch 6" is to provide a passage for the medium (preferably moisture or water) via which the system composed of substrate 1 and coating 4 is tested for barrier qualities and swelling behavior.

After application of the "scratch 6", the rear side of the plastic substrate 2 is sealed water-tight, for example with self-adhesive aluminum film. This step is optional and takes place before step d). In the case of complete surface coating, the step may be omitted per se. In principle, it can also take place before step c) or optionally before step b).

Figure 5:
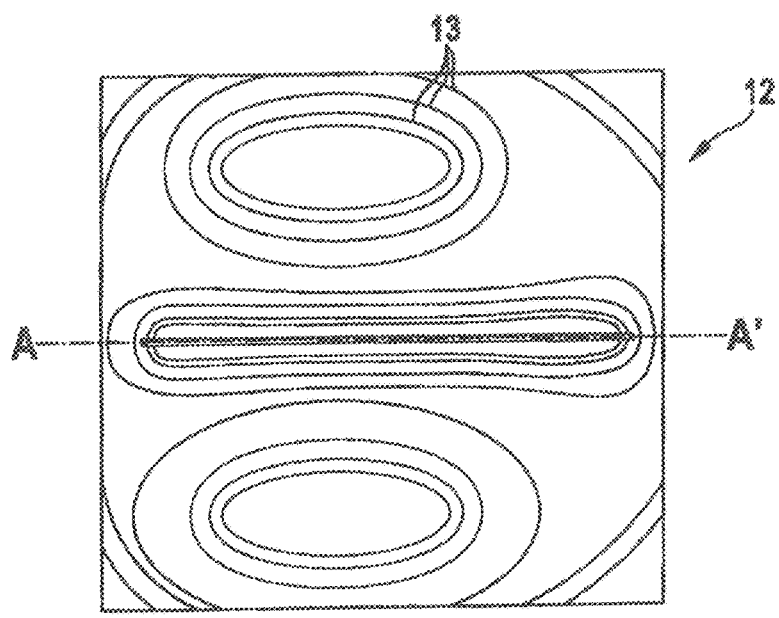
FIG. 5 shows a two-dimensional height profile of the section according to FIG. 4 recorded with an interferometer after swelling of the substrate has occurred.
Figure 6:
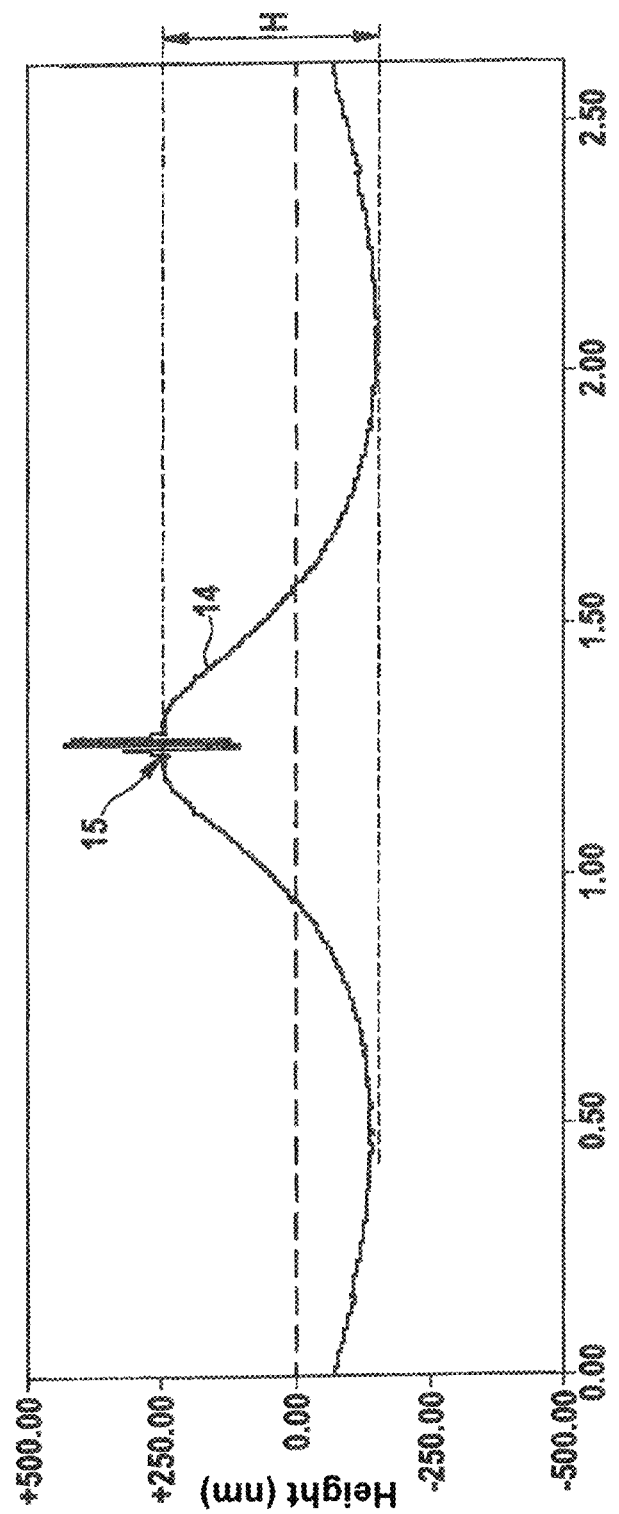
FIG. 6 shows a section through the height profile according to FIG. 5 in the middle of the scratch.

Step f) includes measurement of the swelling or distortion height using an interferometer with which the entire scratch 6 can be measured. The interferometer must have a resolution that allows the height H to be measured over the entire scratch length L, and in the present example in particular, at least a resolution of less than 10 nm. FIG. 5 shows a two-dimensional height profile of the surface of the section of the spectacle lens blank 12 shown in FIG. 4. Height lines 13 are indicated at 20 nm intervals. FIG. 6 shows the height profile 14 perpendicular to section A-A' through the height profile according to FIG. 5. The abscissa indicates the distance in millimeters. The ordinate shows the height in nanometers with respect to the baseline described in the following.

In order to be able to determine the swelling or distortion height H, that is, the height distance between the substrate material with minimum swelling and the substrate material with maximum swelling (the site of maximum swelling is indicated in FIG. 6 by reference no. 15), the plastic substrate-coating system 1, 4, 12 is placed after the scratch 6 is made in a correspondingly humid atmosphere, for example in a climate with an elevated temperature, for example 40° C., and elevated relative humidity, for example 90%, so that swelling can take place (step e). Before exposure of the plastic substrate-coating system 1, 4, 12 to the warm, humid climate, a first measurement is conducted with the interferometer, the so-called baseline, with respect to which changes in the surface can be recorded. This step is referred to as d) in the general description of the invention.

The spectacle lens blank 12 is now placed for a certain period of time, tailored to the swelling behavior of the plastic 2, in the warm, humid climate and then immediately measured with the interferometer. The warm, humid climatic exposure 16 of the spectacle lens blank 12 with the scratch 6 is shown schematically in FIG. 7A. FIG. 7B shows the height profile 14a of the surface of the spectacle lens blank 12 after exposure in cases in which the coating 4 shows virtually no barrier effect with respect to penetrating moisture, which is indicated in FIG. 7A by arrows of equal length 16 in the area of the scratch 6 and the intact surface 18 of the coating 4.

Warm, humid climatic exposure 17 of a spectacle lens blank 12 with a scratch 6 in its coating 4 showing a certain barrier effect is shown schematically in FIG. 8A. The barrier effect of the coating 4 is indicated by shortened arrows 17 in the area of the virgin coating 4. FIG. 8B shows the height profile 14b of the surface of the spectacle lens blank 12 after exposure to moisture.

After the first measurement, the spectacle lens blank 12 is optionally placed once more for a specified period in the warm, humid climate, after which a further measurement is initiated. The series of measurements is preferably continued until virtually no further change in swelling behavior is observed. Thus the swelling behavior over time is determined, via which one can draw conclusions as to the barrier behavior of the coating 4.

Figure 9:
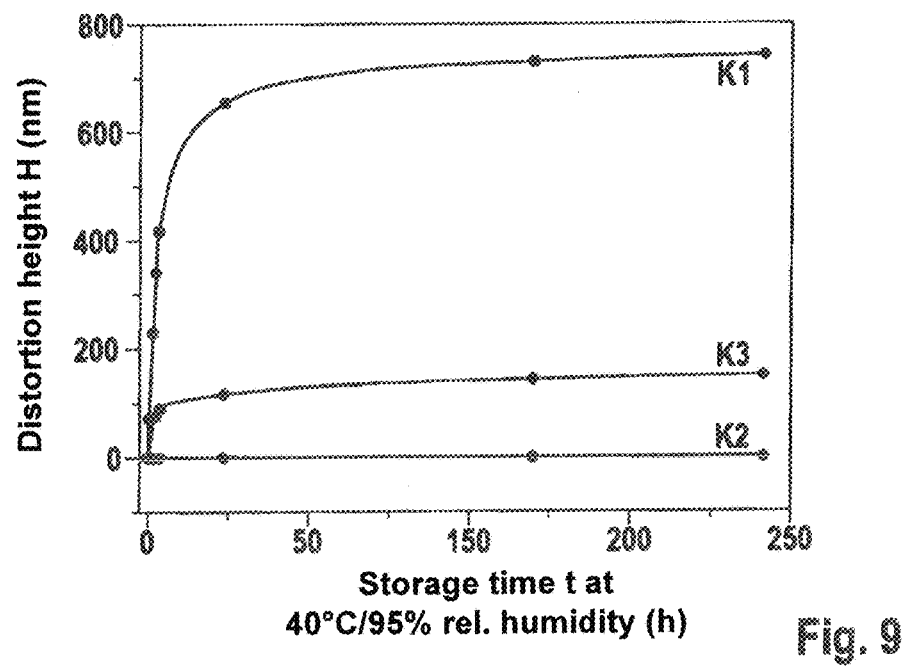
FIG. 9 shows dependency over time of the distortion height H as a function of the storage time t in a warm, humid climate at 40° C. and 95% relative humidity (K1: coating constitutes a total barrier to water; K2: coating constitutes a moderate barrier to water; K3: coating does not constitute a barrier to water)

FIG. 9 shows the time-dependency of the distortion height H as a function of storage duration in a warm, humid climate at 40° C. and 95%, relative humidity. Curve K1 shows the course for a water-impermeable coating 4. Curve K2 shows the course for a coating 4 that allows water to pass unhindered, and curve K3 shows the course over time for a coating having a medium barrier effect. For the coating 4 that constitutes a complete barrier to water, the distortion height H increases exponentially for the first few hours, and reaches a saturation value of approx. 740 nm after approx. 100 hours. For the coating 4 that does not constitute a barrier to water, no distortion can be detected. The third coating 4 according to K3 shows distortion behavior over time similar to that of a coating 4 constituting a complete barrier to water. The saturation value of the distortion height H, however, is approx. 120 nm.

Figure 10:
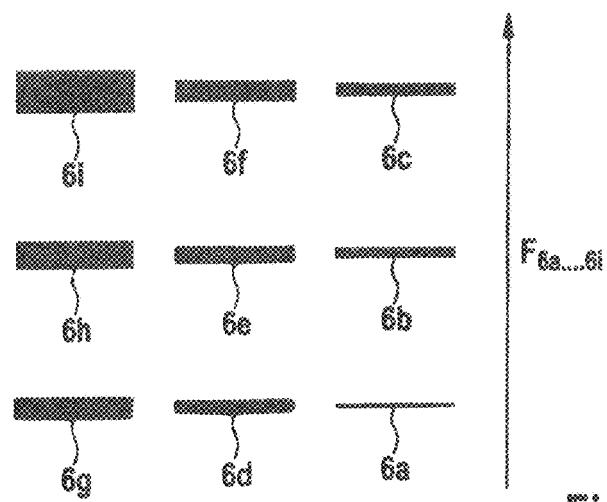
FIG. 10 shows a matrix of scratches according to FIG. 4 made in the surface of a spectacle lens blank with differing loads.
Figure 11:
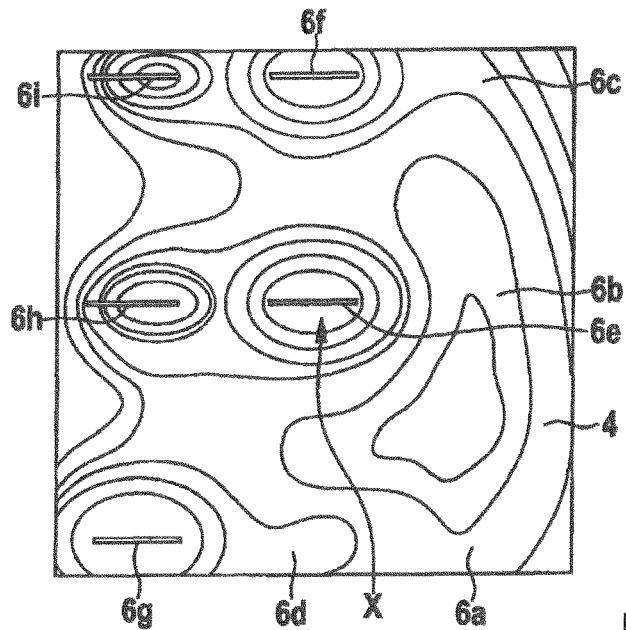
FIG. 11 shows a two-dimensional height profile of the section according to FIG. 10 recorded with an interferometer after exposure of the substrate to a warm, humid climate at 40° C. and 95% relative humidity; and, FIG. 12 shows an illustrative embodiment of a device according to the invention for determining a barrier effect of a coating.

In a further optional step, a series or matrix of scratches 6a, 6b, 6c . . . (FIG. 10) with differing loads $F_{6a}$, $F_{6b}$, $F_{6c}$ . . . is made in the substrate-layer system 1, 4, 12. The loads $F_{6a}$, $F_{6b}$, $F_{6c}$ . . . of the individual scratches 6a, 6b, 6c . . . begin with a load $F_{6a}$ at which the coating 4 is not destroyed and end with the load $F_{6i}$ at which the coating 4 is reliably destroyed. The loads $F_{6b}$, $F_{6c}$, $F_{6d}$ . . . $F_e$, in between are selected in such a way that from a certain load $F_{6e}$ on, a crack 6e is made in the coating. In other words, the coating 4 is subjected to a load $F_{6e}$ such that the deflection produces a crack in the coating. The substrate-coating system 1, 4, 12, as described above, is again placed in the warm, humid climate and measured after a specified period with an interferometer. FIG. 11 shows a two-dimensional height profile of the section according to FIG. 10 recorded with an interferometer after exposure of the substrate to a warm, humid climate of 40° C. and 95% relative humidity.

From a certain load $F_{6e}$ on, at which the coating 4 breaks for the first time, swelling can then take place. The scratch 6e, which was made at breaking load, is indicated in FIG. 11 by the reference sign X. This method can provide data on the breaking load behavior of the coating.

The results obtained can be explained as follows.

The scratch made on the substrate-coating system 1, 4, 12 serves as an entryway for moisture that can be absorbed by the substrate 1 (FIGS. 3 and 4). The substrate 1 is made capable of absorbing moisture by storing the substrate 1 for a sufficiently long time prior to moisture loading in a specified dry climate (conditioning step b).

If the substrate 1 is now loaded with moisture through the scratch, and if the coating 4 constitutes a barrier to moisture, the plastic 2 in the area immediately surrounding the scratch 6 swells to a certain level, which can then be measured with the interferometer as a height line profile (FIG. 5) or as a section through this height line profile (FIG. 6).

If the coating 4 on the substrate 1 is barrier-free with respect to moisture, that is, if moisture can pass through it unhindered, the substrate 1 will swell homogeneously in all areas (FIG. 7B). As a result, no height difference between the scratch 6 and the surrounding area can be measured with the interferometer.

If the coating 4 constitutes a barrier to moisture, more moisture penetrates the substrate 1 at the site of the scratch 6, with the result that a pronounced elevation can be measured at the site of the scratch 6 (FIG. 8B).

There are therefore three different possibilities.

If the coating constitutes a total barrier to the medium (water), this gives rise to a maximum distortion height H (curve K1 in FIG. 9). With no barrier, that is, if the coating 4 allows the medium to pass through unhindered, no distortion can be measured (curve K2 in FIG. 9). In the case of a medium barrier, a curve K3 is obtained that lies between these two curves K1 and K2.

Measurement of swelling behavior over time t according to FIG. 9 and load sensitivity as shown for example in FIG. 11 provide data on the swelling speed, the strength of the barrier effect of the coating 4 with respect to medium moisture, and the sensitivity of the substrate-coating system 1, 4, 12 with respect to medium moisture, thus allowing data to be obtained that correspond to actual behavior in daily application (such as in spectacle lenses).

Figure 12:
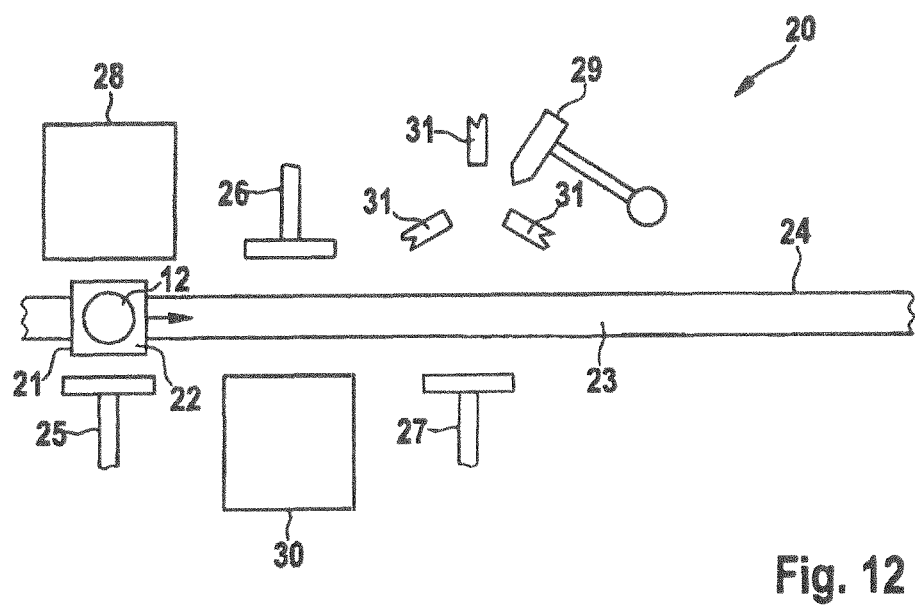

Finally, FIG. 12 shows an illustrative embodiment of a device according to the invention 20 for determining a barrier effect of a coating 4 on a spectacle lens blank 12. The device 20 includes a substrate provision device in the form of a slide 21 with a supporting surface 22. The slide 21 is conured on a conveying device 23 in the form of a conveyor belt 24 having a plurality of sliders 25, 26, 27 in order to allow the slide 21 to be moved from the conveyor belt 24 to various treatment and measuring devices and from there back onto the conveyor belt 24. The various treatment and measuring devices include a conditioning device in the form of a climatic chamber 28, a diamond scratching tool 29, and an interferometer 30.

The device 20 further includes an electronic control device not shown in FIG. 12 for controlling the conveying device 24 and the functions of the other components, specifically the climatic chamber 28, the diamond scratching tool 29, and the interferometer 30.

The device 20 can be operated in the manner described below.

In step a), a spectacle lens blank 12 is provided on the supporting surface 22 of the slide 21. The spectacle lens blank 12 includes a substrate 1 provided with a coating 4 that undergoes a change in volume on contact with water or water vapor.

The slider 25 slides the spectacle lens blank 12 into the climatic chamber 28. In the climatic chamber 28, in accordance with process step b), conditioning of the spectacle lens blank 12 is carried out in the above-described manner by exposure to a standardized climate of 23° C. and 50% relative humidity for 72 hours.

After this period, the spectacle lens blank 12 is moved back to the conveying device 23 via the slider 25. The slide 21 is then moved to the slider 27. The slider 27 slides the slide 21 under the diamond scratching tool 29. The spectacle lens blank 12 is fixed in place on its lateral edge via a three-point gripper 31. Removal of the coating 4 from a first part of the surface of the substrate 1 is then carried out in accordance with step c).

The three-point gripper 31 then places the spectacle lens blank 12 back on the supporting surface 22 of the slide 21, and the slider 27 brings the slide 21 back onto the conveyor belt 24.

The conveyor belt 24 transports the slide 21 with the spectacle lens blank 12 to the slider 26, which then moves the slide 21 for determining a first height profile into the interferometer 30 (step d).

After this, the spectacle lens blank 12 is conveyed in the above-described manner back to the climatic chamber 28. The spectacle lens blank 12 is exposed to a warm, moist climate at 40° C. and 90% relative humidity for 10 minutes (step e). This is followed by conveyance to the interferometer 30, via which, according to step f), a second height profile of the surface of the spectacle lens blank 12 is recorded in the region of the scratch 6 (step f).

The latter steps e) and f) are repeatedly carried out until significant changes in the measured height profile can no longer be detected.

This shows that the above-described method can also be carried out automatically.

It is understood that the foregoing description is that of the preferred embodiments of the invention and that various changes and modifications may be made thereto without departing from the spirit and scope of the invention as defined in the appended claims.

What is claimed is:

1. A method for determining a barrier effect of a coating for a medium, the method comprising the steps of:
   a) providing a substrate with the coating on its surface, which on contact with the medium undergoes a change in volume, or
   providing the coating on a surface of a substrate, which on contact with the medium undergoes a change in volume;
   b) conditioning of the substrate with the coating;
   c) removing the coating from a first part of the surface of the substrate, with the coating remaining on a second part of the
   surface of the substrate, and with the first part of the surface having an extension (L) in a first direction delimited by the coating remaining on the second part of the surface;
   d) determining a first height profile of a surface of the coating remaining on the second part of the surface and the first part of the surface of the substrate on a path in the first direction;
   e) exposing the surface of the remaining coating and the first part of the surface of the substrate to the medium; and,
   f) determining at least one of a second height profile of the surface of the coating remaining on the second part of the surface and the first part of the surface of the substrate on the path in the first direction after performing step e) and a first height profile difference (H) of the surface of the coating remaining on the second part of the surface and the first part of the surface of the substrate on the path in the first direction with respect to the previously-determined height profile.

2. The method of claim 1, wherein said removing the coating according to step c) is carried out using a scratching tool.

3. The method of claim 1, wherein said removing the coating according to step c) is carried out using a diamond scratching tool, which is guided in the first direction to remove material.

4. The method of claim 1, wherein the first part of the surface has an extension (B) in a second direction and the extension (L) of the first part of the surface in the first direction is at least ten times greater than the extension (B) of the first part of the surface in the second direction.

5. The method of claim 1 further comprising the step of: providing a third part of the surface that is not identical to the first part of the surface of the substrate but is coating-free with a barrier that is impermeable to the medium prior to the determining of the first height profile of step d).

6. The method of claim 1, wherein at least one of the determining of the first height profile according to step d), the determining of at least one of the second height profile and the first height profile difference according to step f) is carried out using an interferometer.

7. The method of claim 1, wherein the series of steps e) and f) is carried out repeatedly.

8. The method of claim 7, wherein the series of steps e) and f) is carried out repeatedly until a termination criterion is fulfilled.

9. The method of claim 8, wherein the termination criterion for cases in which a first height profile difference (H) is determined in step f) is that the first height profile difference (H) must be below a specified threshold value.

10. The method of claim 1, wherein the removal of the coating in step c) is carried out completely down to the surface of the substrate.

11. The method of claim 1, wherein the series of steps c) through f) is repeatedly carried out locally in parallel; wherein the removal of the coating in the respective steps c) in the series carried out locally in parallel is carried out to differing degrees.

12. The method of claim 11, wherein the removal of the coating in the respective steps c) in the series carried out locally in parallel is carried out under differing loads.

13. The method of claim 11, wherein the removal of the coating in one of the respective steps c) in the series carried out locally in parallel is carried out all the way to the surface of the substrate.

14. The method of claim 11, wherein the removal of the coating in at least one of the respective steps c) in the series carried out locally in parallel is not carried out all the way to the surface of the substrate.

15. An apparatus for determining a barrier effect of a coating, the apparatus comprising:
   a provision device configured to provide at least one of a substrate with the coating on its surface, which on contact with
   a medium undergoes a change in volume and a coating on a substrate, which on contact with the medium undergoes a change in volume;
   a conditioning device configured to condition the substrate with the coating;
   a removal device configured to remove the coating from a first part of the surface of the substrate, so that the coating remains on a second part of the surface of the substrate and so that the first part of the surface has an extension (L) in a first direction delimited by the coating remaining on the second part of the surface;
   a determination device configured to determine a first height profile of a surface of the coating remaining on the second part of the surface and the first part of the surface of the substrate on a path in the first direction;
   an exposure device configured to expose the surface of the remaining coating and the first part of the surface of the substrate to the medium; and,
   said determination device being further configured to determine at least one of a second height profile of the surface of the coating remaining on the second part of the surface and the first part of the surface of the substrate on the path in the first direction after the medium exposure to the surface and a first height profile difference (H) of the surface of the coating remaining on the second part of the surface and the first part of the surface of the substrate on the path in the first direction with respect to the previously-determined height profile.

16. A computer program with program code stored on a non-transitory computer readable medium, the program code being configured to, when the computer program is loaded onto a computer and/or run on a computer that controls an apparatus, perform a method comprising the steps of:
   a) providing a substrate with the coating on its surface, which on contact with the medium undergoes a change in volume, or providing the coating on a surface of a substrate, which on contact with the medium undergoes a change in volume;
   b) conditioning of the substrate with the coating;
   c) removing the coating from a first part of the surface of the substrate, with the coating remaining on a second part of the surface of the substrate, and with the first part of the surface having an extension (L) in a first direction delimited by the coating remaining on the second part of the surface;
   d) determining a first height profile of a surface of the coating remaining on the second part of the surface and the first part of the surface of the substrate on a path in the first direction;
   e) exposing the surface of the remaining coating and the first part of the surface of the substrate to the medium; and,
   f) determining at least one of a second height profile of the surface of the coating remaining on the second part of the surface and the first part of the surface of the substrate on the path in the first direction after performing step e) and a first height profile difference (H) of the surface of the coating remaining on the second part of the surface and the first part of the surface of the substrate on the path in the first direction with respect to the previously-determined height profile.

* * * * *

UNITED STATES PATENT AND TRADEMARK OFFICE
CERTIFICATE OF CORRECTION

PATENT NO. : 9,778,170 B2
APPLICATION NO. : 15/470537
DATED : October 3, 2017
INVENTOR(S) : Andreas Neuffer Page 1 of 1

It is certified that error appears in the above-identified patent and that said Letters Patent is hereby corrected as shown below:

In the Specification

In Column 10:
Line 16: delete "$F_e$" and substitute -- $F_{6h}$ -- therefor.

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*